United States Patent [19]

Blechschmitt et al.

[11] 4,096,094

[45] Jun. 20, 1978

[54] SUPPORTED CATALYSTS CONTAINING VANADIUM PENTOXIDE AND TITANIUM DIOXIDE

[75] Inventors: Kurt Blechschmitt, Schifferstadt; Peter Reuter, Bad Duerkheim; Friedrich Wirth, Ludwigshafen, all of Germany

[73] Assignee: BASF Aktiengesellschaft, Ludwigshafen am Rhein, Germany

[21] Appl. No.: 730,827

[22] Filed: Oct. 8, 1976

[30] Foreign Application Priority Data

Oct. 24, 1975 Germany .............................. 2547624

[51] Int. Cl.² ........................ B01J 23/04; B01J 23/18; B01J 23/22; B01J 21/06
[52] U.S. Cl. .................................... 252/440; 252/476; 260/346.4
[58] Field of Search ....................... 252/461, 476, 440; 260/346.4

[56] References Cited

U.S. PATENT DOCUMENTS

| 1,909,354 | 5/1933 | Jaeger ................. 260/346.4 |
| 3,909,457 | 9/1975 | Friedrichsen et al. ........... 252/476 |
| 4,007,136 | 2/1977 | Blechschmitt et al. ........... 252/476 |

*Primary Examiner*—W. J. Shine
*Attorney, Agent, or Firm*—Keil, Thompson & Shurtleff

[57] ABSTRACT

A supported catalyst for the oxidation of aromatic or unsaturated aliphatic hydrocarbons, comprising an inert nonporous carrier to which is applied a thin layer of a catalytic composition which contains from 1 to 39.9 percent by weight of vanadium pentoxide, from 60 to 98.9 percent by weight of titanium dioxide and from 0.1 to 10% by weight of rubidium and antimony in an atomic ratio Rb : Sb of from 1:2.5 to 1:30, the vanadium pentoxide content being from 0.05 to 4 percent by weight, based on the supported catalyst.

3 Claims, No Drawings

SUPPORTED CATALYSTS CONTAINING VANADIUM PENTOXIDE AND TITANIUM DIOXIDE

The present invention relates to new supported catalysts containing vanadium pentoxide, titanium dioxide, rubidium and antimony, and to their use for the manufacture of phthalic anhydride by oxidation of o-xylene and/or naphthalene with air.

The use of supported catalysts containing vanadium pentoxide and titanium dioxide as oxidation catalysts for the manufacture of carboxylic acids or carboxylic acid anhydrides by oxidizing aromatic or unsaturated aliphatic hydrocarbons in the gas phase has been disclosed. Catalysts of the said type, which consist of a spherical inert carrier to which is applied a thin layer of a catalytic composition comprising vanadium pentoxide and titanium dioxide are described in, for example, German Pat. No. 1,442,590. They have attained importance in industrial processes for the continuous manufacture of phthalic anhydride from o-xylene or naphthalene.

Catalysts which contain small amounts of sodium or potassium and of antimony in the catalytic composition have also already been proposed, in German Laid-Open Application No. 2,260,615.

These conventional catalysts only attain their optimum effectiveness, in respect of yield and achievable throughput, after a certain period of operation. Furthermore, the yield and throughput achieved with such catalysts leave room for improvement.

It is an object of the present invention to provide supported catalysts which attain their optimum effectiveness soon after the start of the oxidation reaction and furthermore make it possible to achieve a higher yield and throughput.

We have found that this object is achieved and that a supported catalyst, suitable for the oxidation of aromatic or unsaturated aliphatic hydrocarbons, and comprising an inert non-porous carrier and a thin layer, applied thereto, of a catalytic composition which contains from 1 to 39.9 percent by weight of vanadium pentoxide and from 60 to 98.9 percent by weight of titanium dioxide, and has a vanadium pentoxide content, based on the supported catalyst, of from 0.05 to 4 percent by weight, exhibits these desirable advantageous properties if the catalytic composition contains from 0.1 to 10 percent by weight of rubidium and antimony in an atomic ratio Rb:Sb of from 1:2.5 to 1:30.

The inert non-porous carrier present in the new catalysts consists of sintered or fused silicates, porcelain, silicon carbide, rutile or quartz. The carrier is advantageously in the shape of spheres of diameter from 3 to 12 mm, or in the shape of rings.

The catalytic composition applied to the carrier is in the form of a layer which is, for example, from 0.03 to 1 mm thick and preferably from 0.05 to 0.4 mm thick. The active composition accounts for from about 3 to 50 percent by weight of the supported catalyst.

The titanium dioxide used is advantageously in the form of anatase having an internal surface area of from 5 to 50 $m^2/g$, preferably from 5 to 20 $m^2/g$, and a particle size of less than 1 $\mu m$, for example from 0.4 to 0.8 $\mu m$. The content of rubidium and antimony in the active composition is from 0.1 to 10 percent by weight, preferably from 0.5 to 5 percent by weight. The atomic ratio of rubidium to antimony is from 1:2.5 to 1:30, preferably from 1:10 to 1:20.

The required content of rubidium and antimony in the active composition is achieved by adding appropriate amounts of rubidium compounds and antimony compounds to the active composition. Examples of suitable rubidium compounds are the oxide, hydroxide, carbonate, acetate, nitrate, vanadate or sulfate. In the course of the manufacture of the catalyst these compounds — except for the sulfate, vanadate and oxide, which remain unchanged — are converted to the oxide so that in the finished catalyst the rubidium is in the form of rubidium oxide, rubidium vanadate or rubidium sulfate. Examples of suitable antimony compounds are antimony tetroxide, antimony trioxide, antimony sulfate, antimony vanadate and ammonium antimony-III-tartrate. In the finished catalyst, the antimony is in the form of antimony trioxide, antimony vanadate or antimony sulfate.

The catalyst is manufactured by applying the active composition to the carrier by conventional methods. For example, vanadium pentoxide, or a vanadium compound which on heating is converted to vanadium pentoxide, such as ammonium vanadate, or vanadium oxalate, formate, acetate, tartrate or salicylate, is mixed with the finely divided titanium dioxide, with addition of the stated rubidium compound and antimony compound, in water or an organic solvent, e.g. formamide, ethanolamine, diethylacetamide or an alkanol, and the mixture, which in most cases is pasty, is sprayed, for example in a coating drum, onto the carrier which has been preheated at 100° - 450° C. The finely divided titanium dioxide is obtained by, for example, milling, advantageously in a colloid mill. Subsequent heating of the coated catalyst carrier, for example at from 200° to 500° C, under oxidizing or reducing conditions, can be of advantage when manufacturing the catalyst. For this purpose the catalyst is heated, for example, in the presence of a mixture of o-xylene and air or of a mixture of air and sulfur dioxide.

The new catalysts can be used for the manufacture of carboxylic acids or carboxylic acid anhydrides by oxidizing aromatic or unsaturated aliphatic hydrocarbons in the gas phase, e.g. for the manufacture of phthalic anhydride by oxidizing o-xylene and/or naphthalene with air, or for the manufacture of pyromellitic anhydride by oxidizing durene or other 1,2,4,5-tetraalkylbenzenes with air. The oxidation reaction is carried out in a manner which is in itself known.

When used for the manufacture of phthalic anhydride, the new supported catalyst is placed, for example, in a tube furnace, wherein the tubes have a diameter of from 18 to 40 mm and a length of from 1 to 4.0 m, and is brought into contact with the gaseous mixture of o-xylene and/or naphthalene and air. It is advantageous to use catalyst carriers which have a diameter which is about one-third of the internal diameter of the tubes used.

To regulate the temperature, the tubes are surrounded by a salt melt which is kept at from 360° to 450° C. The hourly throughput per liter of catalyst is in general from 2 to 8 cubic meters (S.T.P.) of air, laden with up to 100 g of hydrocarbon per cubic meter (S.T.P.).

EXAMPLE (a) Manufacture of catalyst I according to the invention 600 g of steatite rings having an external diameter of 8 mm, a length of 6 mm and a wall thickness of 1.5 mm are heated at 260° C in a coating drum and are sprayed with a suspension consisting of 400 g of anatase, having an internal surface area of 11 m²/g, 73.2 g of vanadyl oxalate (having a vanadium content corresponding to 41% of $V_2O_5$), 500 g of water, 100 g of formamide, 0.55 g of rubidium carbonate and 10.75 g of antimony trioxide until the weight of catalytic composition applied is 10% of the total weight of the catalyst. The vanadium pentoxide content of the supported catalyst is 0.64% by weight.

The catalytic composition contains 2.15% by weight of rubidium and antimony, based on titanium dioxide and vanadium pentoxide. The atomic ratio of rubidium to antimony is 1:15.7.

(b) Comparative catalyst II

Catalyst II is manufactured like catalyst I, but without adding rubidium carbonate to the suspension.

(c) Comparative catalyst III

Catalyst III is manufactured like catalyst I, but without adding antimony trioxide to the suspension.

(d) Oxidation

A 3.20 m long iron tube having an internal width of 25 mm and surrounded by a salt melt to regulate its temperature is filled to a length of 2.80 m with catalyst I. Per hour, 4.5 cubic meters (S.T.P.) of air, containing per cubic meter up to 42 g of 97% strength by weight o-xylene, are passed through the tube. Catalysts II and III are tested under the identical conditions in two further iron tubes.

The results summarized in the Table which follows are obtained with the catalysts (the yields quoted are the phthalic anhydride obtained in % by weight, based on 100% strength o-xylene or naphthalene):

| Duration of operation days | Yield of phthalic anhydride in % by weight | | |
|---|---|---|---|
| | Catalyst I | Catalyst II | Catalyst III |
| 10 | 104.2 | 98.5 | 98.9 |
| 20 | 106.0 | 100.5 | 101.5 |
| 30 | 107.3 | 103.1 | 105.5 |
| 50 | 111.2 | 105.2 | 107.4 |
| 70 | 112.9 | 107.2 | 110.2 |
| 100 | 114.1 | 108.1 | 111.0 |
| 130 | 113.8 | 108.8 | 110.5 |
| 150 | 114.2 | 108.5 | 110.8 |

We claim:
1. A supported catalyst for the oxidation of aromatic or unsaturated aliphatic hydrocarbons, comprising an inert nonporous carrier to which is applied a layer of a catalytic composition which contains from 1 to 39.9 percent by weight of vanadium pentoxide and from 60 to 98.9 percent by weight of titanium dioxide, with a vanadium pentoxide content based on the supported catalyst of from 0.05 to 4 percent by weight, wherein the catalytic composition also contains from 0.1 to 10 percent by weight total of rubidium in the form of rubidium oxide, rubidium vanadate or rubidium sulfate and antimony in the form of antimony trioxide, antimony vanadate, or antimony sulfate in an atomic ratio Rb:Sb of from 1:2.5 to 1:30.

2. A supported catalyst as claimed in claim 1, wherein the catalytic composition contains from 0.5 to 5 percent by weight total of rubidium and antimony.

3. A supported catalyst as claimed in claim 1, wherein the atomic ratio of rubidium to antimony is from 1:10 to 1:20.

* * * * *